United States Patent [19]

van Heusden et al.

[11] 4,130,758
[45] Dec. 19, 1978

[54] DEVICE FOR DETERMINING GASEOUS COMPONENTS

[75] Inventors: Sybrandus van Heusden; Leonardus P. J. Hoogeveen, both of Eindhoven, Netherlands

[73] Assignee: U.S. Philips Corporation, New York, N.Y.

[21] Appl. No.: 789,100

[22] Filed: Apr. 20, 1977

[30] Foreign Application Priority Data

Apr. 21, 1976 [NL] Netherlands .......................... 7604197

[51] Int. Cl.² .............................................. G01T 1/20
[52] U.S. Cl. .................................................. 250/361 C
[58] Field of Search .................................... 250/361 C

[56] References Cited

U.S. PATENT DOCUMENTS 3,726,599  4/1973  Neary .............................. 250/361 C
3,746,513  7/1973  Warnick et al. ................. 250/361 C

FOREIGN PATENT DOCUMENTS 2501993  8/1975  Fed. Rep. of Germany ....... 250/361 C Primary Examiner—Alfred E. Smith
Assistant Examiner—Janice A. Howell
Attorney, Agent, or Firm—Thomas A. Briody

[57] ABSTRACT

Device for determining the concentration of vaporous components in a gas current, wherein the gas current reacts in a heated reaction room with ozon and the intensity of the chemiluminescent radiation emitted herewith is measured by a photoelectric cell.

5 Claims, 1 Drawing Figure

U.S. Patent
Dec. 19, 1978
4,130,758
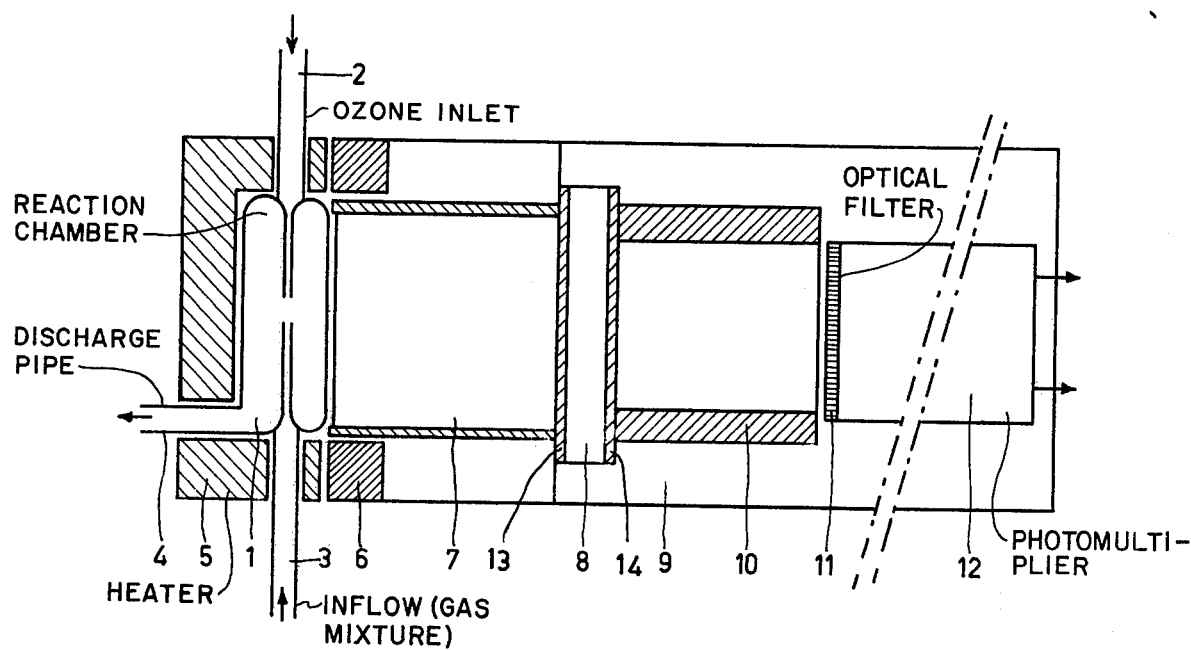

DEVICE FOR DETERMINING GASEOUS COMPONENTS

The invention relates to a device for determining the concentration of vaporous components in a gas current.

An article by W. Bruening and F. J. M. Concha in the "Journal of Chromatography", Vol. 112, pages 253–265 (1975) discloses such a device with which the concentration of a plurality of vaporous components is determined in a reaction room wherein reaction with ozone takes place at an elevated temperature. In this reaction a portion of the energy is released in the form of chemiluminescent radiation. There is a dependency of the sensitivity of these reactions as a function of the temperature. The authors use this for obtaining a given selectivity as regards certain classes of reactive compounds and to obtain a low detection limit. They found that at a temperature of 300° C. both alkanes and alkenes have a useful sensitivity in the chemiluminescent emission and that at temperatures below 150° C. alkanes have a negligibly small sensitivity. The detector was connected to the gaschromatograph.

Applicants found that at temperatures which were varied between room temperature and 350° C. many classes of compounds show an increasing sensitivity as compared with that at room temperature.

Besides the classes investigated by the above-mentioned authors, also cyclo-alkanes, alcohols, aromatic hydrocarbons an substituted aromatic compounds. alkynes, ethers, amines, mercaptans, hydrogen sulphide, chloroform, vinylchloride, carbon monoxide, nitrogen monoxide and hydrogen appear to show such a behaviour.

The device described in the above-mentioned article is, however, rather complicated. Supply pipes for ozone and the carrier gas current of the gaschromagraph end in the reaction chamber which comprises means for heating it, which gases are pre-heated before flowing into the chamber. In the experiments which resulted in the invention the maximum sensitivity of the reaction appeared to occur at the moment the reagent is introduced at room temperature and that the mixture is not heated to the desired reaction temperature until in situ contact with the reactant. This is desirable to limit the loss of active reagent when it contacts hot walls.

In addition, the reaction chamber in the prior art device is made of metal which makes it vulnerable to corrosion, whereafter the oxidation products may produce unwanted phenomena.

The device according to the invention consists of a reaction chamber, a photoelectric measuring cell and means for accommodating at least one optical filter for any desired limitation of the wavelength range to be measured. The reaction chamber comprises an inlet pipe for ozone, an inlet for the gas mixture to be analyzed, which two inlets have their exhaust ends close to one another, an outlet for the gases whose reaction has finished, and means for heating the reaction chamber.

Preferably the reaction chamber is constructed of glass, coated on the outside with reflecting material, or it consists of metal which has been made inert. It is advantageous that the inlet for the mixture to be analyzed and that for the ozone gas face one another.

The accompanying drawing shows diagrammatically a preferred embodiment of the device according to the invention. In the device, the reaction chamber 1 has an inlet 2 for ozone, which is prepared by means of a silent discharge (6kV) in an oxygen current of 80 ml/min. The ozone concentration in the gas current is approximately 0.1%. The device has an inflow 3 through which the mixture to be analyzed is provided in an air current at a flow rate of 70 ml/min.

The reactive gases are removed through a discharge pipe 4. The reaction chamber 1 is heated by means of heating tape 5. The light emitted by the chemiluminescent reation is incident through a cylinder 7 which is coated with reflective material, two quartz glass windows 13, 14, mounted in a ring 8, the cylinder 10 which is coated with reflecting material and one or more optical filters mounted in ring 11 onto the photomultiplier tube 12. This tube is accommodated together with the light pipes in a thermoelectrically cooled casing 9. A ring 6 of asbestos is disposed between the reaction room and the photomultiplier tube casing 9 for the purpose of thermal insulation.

The device according to the invention can be used as a detector with a gas chromatograph column, as already described in the above-mentioned article. In a realized embodiment a detection limit of some p.p.b. ($10^{-7}$ vol.%) was obtained for hydrocarbons at a temperature of 250° C.

The device may also be used as monitor, that is to say, as a detector for one given component wherein the other components, which disturb the reaction, are removed by an adsorption filter. An example hereof is the detection of carbon monoxide in a mixture of hydrocarbons. The reaction with ozone takes place at a temperature of 150°–300° C. As other hydrocarbons also give an emission, they are removed in advance by means of an adsorption filter filled with, for example, "Porapak S", a polystyrene polymer. Methane is not adsorbed by this filter but its chemiluminescent emission is negligible. A CO-monitor constructed in this way had a detection limit in the order of $10^{-7}$ vol.% (1 p.p.b.).

When the device is used for measuring, for example, NO or sulphur compounds interference by disturbing components can be suppressed by using an optical filter, so that chemical filtering can be dispensed with. For the NO measurement a detection limit of 0.5 p.p.b. ($0.5 \times 10 - 7$ vol.%) is reached at a temperature of 285° C.

Finally, it is possible to perform by means of the device according to the invention a determination of the reactivity of the mixture of hydrocarbons which play a part in smog formation within the frame work of measurements for monitoring air pollution. In this determination no pre-separation is used. The device is adjusted to such a temperature that a signal is obtained which corresponds with the reactivity of the relevant hydrocarbons during the smog formation process.

Further details of measurements by means of the device according to the invention are described in an article which has been published in the meantime by the inventors in Z. Anal. Chem. 282, 307–313 (1976).

What is claimed is:

1. A device for determining the concentration of vaporous components in a gas current, comprising
   (a) a reaction chamber, comprising an inlet pipe for ozone, an inlet for the gas mixture to be analyzed, which inlets end close to one another, a discharge for the reacted gases and means for heating the reaction chamber, wherein said device is constructed such that the ozone is introduced so that heating of the ozone does not take place until said ozone is in situ for the reaction,
   (b) a photoelectric measuring cell and (c) means for interposing at least one optical filter.

2. A device as in claim 1, wherein said reaction chamber is made of glass coated on the outside with reflecting material.

3. A device as in claim 1, wherein said reaction chamber consists of metal which has been made inert.

4. A device as in claim 1, wherein said inlet for the mixture to be analyzed and that for the ozone gas face one another.

5. A method of determining the photochemical reactivity of a mixture of hydrocarbons which is involved in the formation of smog, by mixing same with ozone in a device as recited in claim 1, wherein the reaction is allowed to take place at such a temperature that a signal is obtained which corresponds with the reactivity of the relevant hydrocarbons during smog formation.

* * * * *